United States Patent [19]

Clavell

[11] Patent Number: 4,913,648
[45] Date of Patent: Apr. 3, 1990

[54] QUARTZ BURNER:FOR USE IN AN ATOMIC ABSORPTION SPECTROMETER FOR THE ANALYSIS OF ORGANOMETAL COMPOUNDS VIA HYDRIDE DERIVATIZATION

[75] Inventor: Cesar Clavell, San Diego, Calif.

[73] Assignee: The United States of America as represented by the Secretary of the Navy, Washington, D.C.

[21] Appl. No.: 290,738

[22] Filed: Dec. 27, 1988

[51] Int. Cl.⁴ ............................................... F23D 5/12
[52] U.S. Cl. ..................................... 431/13; 239/428; 239/433; 356/315
[58] Field of Search ................ 431/13, 354; 137/551; 356/51, 315; 48/189.1; 422/55, 89, 91

[56] References Cited

U.S. PATENT DOCUMENTS

| | | | |
|---|---|---|---|
| 4,220,413 | 9/1980 | Targowski et al. | 356/315 |
| 4,277,254 | 7/1981 | Hanson | 48/180 R |
| 4,311,664 | 1/1982 | Zaremba et al. | 422/54 |
| 4,432,286 | 2/1984 | Witte | 431/13 X |
| 4,508,685 | 4/1985 | Sisti et al. | 422/54 |
| 4,640,677 | 2/1987 | Huber | 431/89 |

FOREIGN PATENT DOCUMENTS 194226 10/1985 Japan ..................................... 431/13

OTHER PUBLICATIONS

Presented and Published at the Proceedings of the Organotin Symposium of the Oceans 86 Conference and Exposition, Wash., D.C., 23–25, Sep. 1986, "Automated Analysis of Organotin Compounds: A Method for Monitoring Butyltins in the Marine Environment", Cesar Clavell et al.

Primary Examiner—Randall L. Green
Attorney, Agent, or Firm—Harvey Fendelman; Thomas Glenn Keough

[57] ABSTRACT

The atomic constituents of volatile organic compounds are determined by a burner design having improved stability and, consequently, increased detection sensitivity. An optical window is included at one end of a burner tube to stabilize a hydrogen-air flame to avoid blow out. Since air and combined air and helium are introduced immediately in front of the window and the flow rate of the gases and a sample are particularly oriented, burning is complete for increased detection sensitivity by an interconnected atomic absorption spectrophotometer.

4 Claims, 2 Drawing Sheets

QUARTZ BURNER:FOR USE IN AN ATOMIC ABSORPTION SPECTROMETER FOR THE ANALYSIS OF ORGANOMETAL COMPOUNDS VIA HYDRIDE DERIVATIZATION

STATEMENT OF GOVERNMENT INTEREST

The invention described herein may be manufactured and used by or for the United States of America for governmental purposes without the payment of any royalties thereon or therefor.

BACKGROUND OF THE INVENTION

An automated laboratory procedure for the determination of several environmentally important organotin compounds is set out in detail in a paper presented and published at the Proceedings of the Organotin Symposium of the Oceans 86 Conference and Exposition, Washington, D.C., Sept. 23-25, 1986. This automated analysis utilizes hydride derivatization directly in seawater yielding volatile mono-, di- and tributyltin species which can be concentrated sufficiently to assure their detection. This analysis apparatus is schematically shown in FIG. 1 of the drawings for the speciation of trace organotin compounds. The method employs hydride derivatization directly in seawater yielding the volatile mono-, di- and tributyltin hydride species. The tin hydrides from a one liter sample are concentrated in a cryogenic trap "a" coupled to a liquid nitrogen source "b". Eletrothermal heating of trap "a" volitolizes the hydride compounds in a hydrogen flame burner 10 enabling the detection of the compounds of interest via an atomic absorption spectrophotometer "c". A controller "d" relies on an IBM-PC or compatible PC equipped with interface electronics for I/O control. Software is written in the Poly FORTH language which provides a multiuser multitasking environment.

This computer control, among other things, controls an analytical section including a reagent addition unit "e". A pump "f" draws a seawater sample at "In", and transfers the sample into a hydride reaction vessel "h". Appropriate valving and the addition of helium channels the reaction product to trap assembly "a" which is under control of computer "d".

Atomic absorption spectrophotometer "c" is a standard Buck instruments model 200 and has a sensitivity that is adequate for most butyltin monitoring requirements. Hydrogen and air were added to the concentrated reaction product coming into the burner and the appropriate analysis was made in accordance with the established procedures for the spectrophotometer. A thorough understanding of the operation of this analytical apparatus is set forth in the above cited publication.

SUMMARY OF THE INVENTION

The present invention is directed to providing a burner for use in an atomic absorption spectrophotometer for the analysis of organotin compounds via hydride derivatization. An appropriate arrangement of fused together quartz tubelets passes hydrogen, air and an organic compound sample into a combustion chamber provided with a window that is adjacent a hydrogen-air flame. This creates an environment which is capable of completely disassociating volatile organic compounds into their atomic constituents. The location of the optical window and the tubelets for the hydrogen, air, helium and organic compound assures the complete disassociation even at low flow rates to thereby increase the detection sensitivity of the associated equipment.

An object of the invention is to provide an improvement over a conventional sample atomizer in an atomic absorption spectrophotometer.

Another object is to provide a burner design configured to stabilize a hydrogen-air flame to reduce the possibility of flame blow out.

Another object is to provide a burner design which reduces the tendency for a hydrogen-air flame to blow out at low flow rates and eliminates the requirement for external heating.

Still another object of the invention is to provide for a burner specifically configured to increase the detection sensitivity for mono-butyltin, di-butyltin and tributyltin compounds.

These and other objects of the invention will become more readily apparent from the ensuing specifications when taken in conjunction with the attached drawings and the appended claims.

DESCRIPTION OF THE PREFERRED EMBODIMENT

Figure 1:
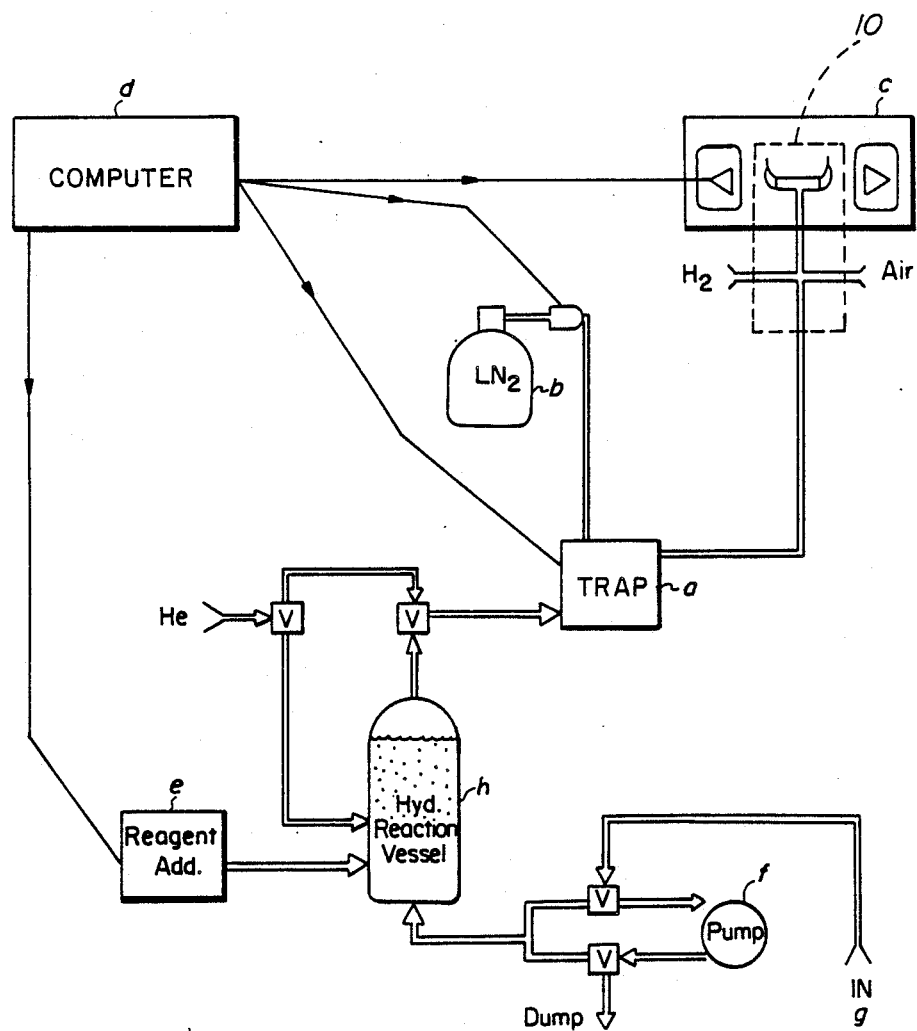
FIG. 1 shows a schematic diagram of a state of the art automated organotin analyzer for including the present inventive concept.
Figures 2, 3:
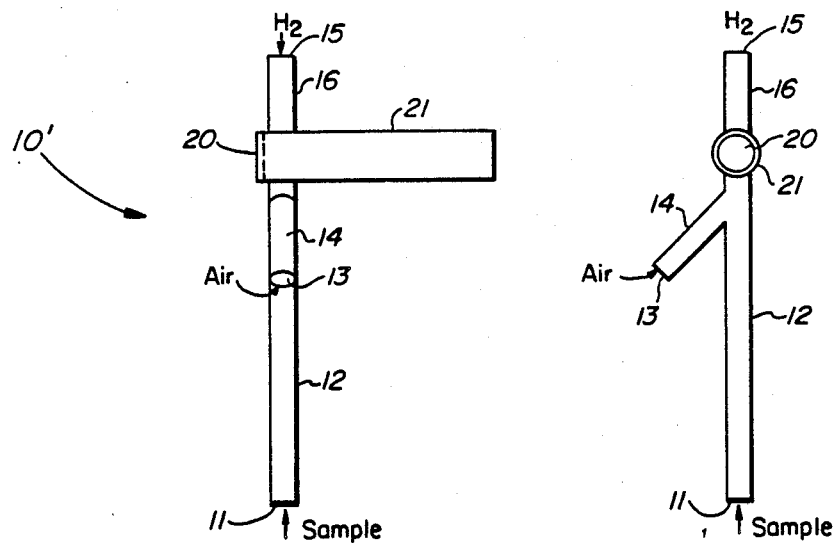
FIG. 2 shows a top view of the invention.
FIG. 3 shows a side view of the invention.

The increased use of tributyltin based anti following paints and the impact on the marine environment have made the development of techniques to measure parts per trillion levels necessary. A burner modification 10' shown in FIGS. 2 and 3, with other modifications to the systems, increased the sensitivity by a factor of about 10.

Samples of tin hydrides enter the burner at an inlet port 11 of an inlet tubelet 12. Predetermined amounts of air are fed through an air inlet port 13 and enter an air inlet arm tube 14 which is disposed at a 45 degree angle relative to tubelet 12. A suitable amount of hydrogen is fed to the burner via an inlet port 15 and a length of tublet 16 which is coextensive with tublet 12. A quartz window 20 is disposed at one end of a quartz burner tube 21 and provides an optical window for the burning occurring on the inside of the burner tube.

Typically, the length of tublet 12 is about 3.25 inches and the length of tublet 16 is about 0.75 inches. Arm tublet 14 is about one inch long and tubelets 12, 13 and 16 have outer diameters of about 0.250 inches. They may be fabricated from quartz so as not to react or otherwise fail with the burning which primarily occurs within burner tube 21. The burner tube has an outer diameter of about 0.5 inches and a length of about 2.375 inches.

The quartz burner design concentrates the evolved tin hydrides into a small area resulting in an intensified signal so that the optical window 20 allows the monitoring of a stabilized hydrogen-air-sample flame. The design reduces the tendency for the flame to blow out at lower flow rates and eliminates the requirement for external heating to keep the flame going. Burner 10' along with trap "a" are periodically flushed with dry helium to remove water vapor when helium is fed through inlet 11 after a particular sample or sequence of samples has been analyzed.

The arrangement of tubelets 12,14 and 16 along with the location and configuration of tube 21 assure a complete mixture of the sample and hydrogen along with air and provides for a stable-contained high temperature environment capable of completely disassociating volatile organic compounds into their atomic constituents.

Figure 4:
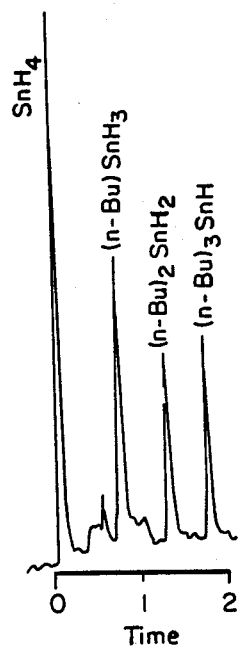
FIG. 4 shows a speciation of butyltins in seawater in which the amount of compounds as the cation is as follows (n-Bu) $Sn+3$ 1.3 ng (n-Bu)$_2$Sn+2 0.64 ng (n-Bu)$_3$Sn+$^1$.3 ng.

The typical result of an analysis of a seawater sample are shown in FIG. 4 in which fairly low butyltin concentrations are depicted. The absolute detection limits were obtained by running a series of blank seawater samples spiked with 0.5 parts per trillion each of mono-, di- and tributyltin chloride. The detection limits based on three sigma of these near background standard additions are 0.180 parts per trillion tributyltin 0.080 parts per trillion di-butyltin and 0.120 parts per trillion monobutyltin calculated as the cation.

The complete disassociating of volatile organic compounds into their atomic constituents is attributed to the burner design. The previous burner designs formed from a straight tube open at each end with gas input located at the center of the tube had allowed the input sample gas stream to enter the tubes centrally and be split to exit from both ends. The disadvantage of this contemporary arrangement is that there was a poor flame stability at low hydrogen-air flow rates. This results in the loss of flame from one end of the tube with a subsequent reduction in detection sensitivity. In addition the use of external heating is required in contemporary systems to guarantee the integrity of the flame. This added requirement increased the cost and complexity of the burner installation and also is a consideration in the element of reliability. In comparison this invention has the optical window at one end of the burner tube to stabilize the hydrogen-air-sample flames and there is no tendency for the flame to blow out at low flame rates. The detection sensitivity for monobutyltin, dibutyltin and tributyltin compounds has been increased by a factor of ten.

Obviously, many modifications and variations of the present invention are possible in light of the above teachings. It is therefore to be understood that within the scope of the inventive claims the invention may be practiced otherwise than is specifically described.

I claim:

1. An improved burner for an atomic absorption spectrophotometer comprising:
    a sample feeder tubelet sized to receive a sample to be analyzed;
    a hydrogen feeder tubelet sized to receive hydrogen;
    an air feeder tubelet sized to receive air and being coupled to the sample feeder tubelet at an acute angle;
    a burning chamber interposed between the sample feeder tubelet and the hydrogen feeder tubelet; and
    an optical window disposed at one end of the burning chamber for permitting monitoring burning in the chamber.

2. An improved burner according to claim 1 in which the sample feeder tubelet and the hydrogen feeder tubelet are aligned and the burning chamber is tube-shaped and orthogonally oriented with respect to the aligned tubelets.

3. An improved burner according to claim 2 in which the optical window laterally extends across the burning chamber at a location where the burning chamber is interposed between the sample feeder tubelet and the hydrogen feeder tubelet.

4. An improvement according to claim 3 in which the angle at which the air feeder tubelet is joined to the sample feeder tubelet assures that the sample and air are mixed thoroughly with the hydrogen for the complete combustion thereof.

* * * * *